United States Patent
Prohaska (12)

(10) Patent No.: US 6,328,721 B1
(45) Date of Patent: Dec. 11, 2001

(54) OSTOMY SUPPORT BELT

(76) Inventor: Joseph Prohaska, 476 Sly Dr., Winnipeg Manitoba (CA), R2V 2H4

( * ) Notice: Subject to any disclaimer, the term of this patent is extended or adjusted under 35 U.S.C. 154(b) by 0 days.

(21) Appl. No.: 09/456,574

(22) Filed: Dec. 8, 1999

Related U.S. Application Data

(60) Provisional application No. 60/140,995, filed on Jun. 29, 1999.

(51) Int. Cl.[7] ........................................... A61F 5/44
(52) U.S. Cl. ............................................. 604/338
(58) Field of Search ................... 604/338, 339, 604/340, 341

(56) References Cited

U.S. PATENT DOCUMENTS

| | | | | |
|---|---|---|---|---|
| 3,577,986 | * | 5/1971 | Regent | 128/96 |
| 3,826,262 | * | 7/1974 | Blackwood | 128/283 |
| 4,238,059 | * | 12/1980 | Caraway et al. | 222/529 |
| 4,319,571 | * | 3/1982 | Winchell | 128/DIG. 24 |
| 4,986,824 | * | 1/1991 | Steer et al. | 604/333 |
| 5,423,852 | * | 6/1995 | Daneshvar | 606/201 |
| 5,429,626 | * | 7/1995 | Fenton | 604/339 |
| 5,514,155 | * | 5/1996 | Daneshvar | 606/201 |
| 5,709,674 | * | 1/1998 | Steer | 604/342 |
| 5,843,053 | * | 12/1998 | Steer | 604/342 |

* cited by examiner

Primary Examiner—Manuel Mendez
(74) Attorney, Agent, or Firm—Michael R. Williams; Adrian D. Battison; Ryan W. Dupuis

(57) ABSTRACT

An ostomy belt is described herein. Specifically, the belt is arranged to be worn around the waist of the patient and includes an aperture portion which extends in a downward direction from the line of the belt for connecting an ostomy bag thereto. The aperture portion includes a support member, in one embodiment, a concave steel plate which provides support for the ostomy bag and also supports the abdominal wall, thereby preventing the development of hernias. In one embodiment, the belt is constructed of leather, meaning that the belt is somewhat rigid and will not stretch, meaning that the belt provides greater support and comfort.

1 Claim, 4 Drawing Sheets

OSTOMY SUPPORT BELT

This application claims the benefit of provisional application No. 60/140,995, filed Jun. 29, 1999.

The present invention relates generally to the field of medical garments. More specifically, the present invention relates to an ostomy support belt.

BACKGROUND OF THE INVENTION

As part of treatment for some types of cancer, including colon cancer or rectum cancer, as well as other diseases, for example, ulcerative colitis, it is often necessary for a patient to undergo an enterostomy. This involves making an opening in the intestine through the abdominal wall. An ostomy bag is then connected to the opening to receive fecal material from the intestine.

There are a number of devices known in the prior art for securing and holding the ostomy bag in place. Typically, these devices are composed of an elastic material and in some cases are arranged to be wrapped around the hips of the patient. Furthermore, these devices include an open area arranged to be placed over the opening in the abdominal wall and may include connectors for attaching the ostomy bag thereto.

However, the prior art devices, especially those composed of elastic material, provide inadequate support, as they tend to stretch with use. Furthermore, as these devices are often arranged to be wrapped around the hips of the individual, they limit the movement of the wearer and cause discomfort. These devices are also not arranged to provide support to the abdominal wall while connected to the ostomy bag and as a consequence, the ostomy patient often develops other complications, for example, hernias.

Clearly, an ostomy support belt is needed that provides abdominal support and is comfortable to wear.

SUMMARY OF THE INVENTION

It is therefore an object of the invention to provide an ostomy belt arranged to extend around the waist of an individual, which is also comfortable to wear, provides support for the ostomy bag and prevents the development of hernias.

According to the invention, there is provided an ostomy belt comprising:

a first end having a male connector;

a second end having a female connector;

an open portion between the first end and the second end, said open portion arranged to be centred around an artificial intestinal opening through an abdominal wall; and a support member extending around the open portion, said support member for contacting and supporting the abdomen of the user, wherein the first end and the second end are arranged to be fitted around the waist of an individual and the open portion descends downward from the first end and the second end such that the open portion is beneath the line of the first end and the second end.

The support may be a concave plate.

The plate may be substantially oval and have an open center. That is, the plate may be arranged to be wider on the sides than on the top and bottom.

One embodiment of the invention will now be described in conjunction with the accompanying drawings in which:

BRIEF DESCRIPTION OF THE DRAWINGS

In the drawings like characters of reference indicate corresponding parts in the different figures.

DESCRIPTION OF THE PREFERRED EMBODIMENTS

As used herein, the term "ostomy" refers to all types of procedures wherein a passageway is provided through the skin and a portion of the intestine or stoma is surgically connected thereto for the discharge of fecal matter or for other purposes.

Figure 1:
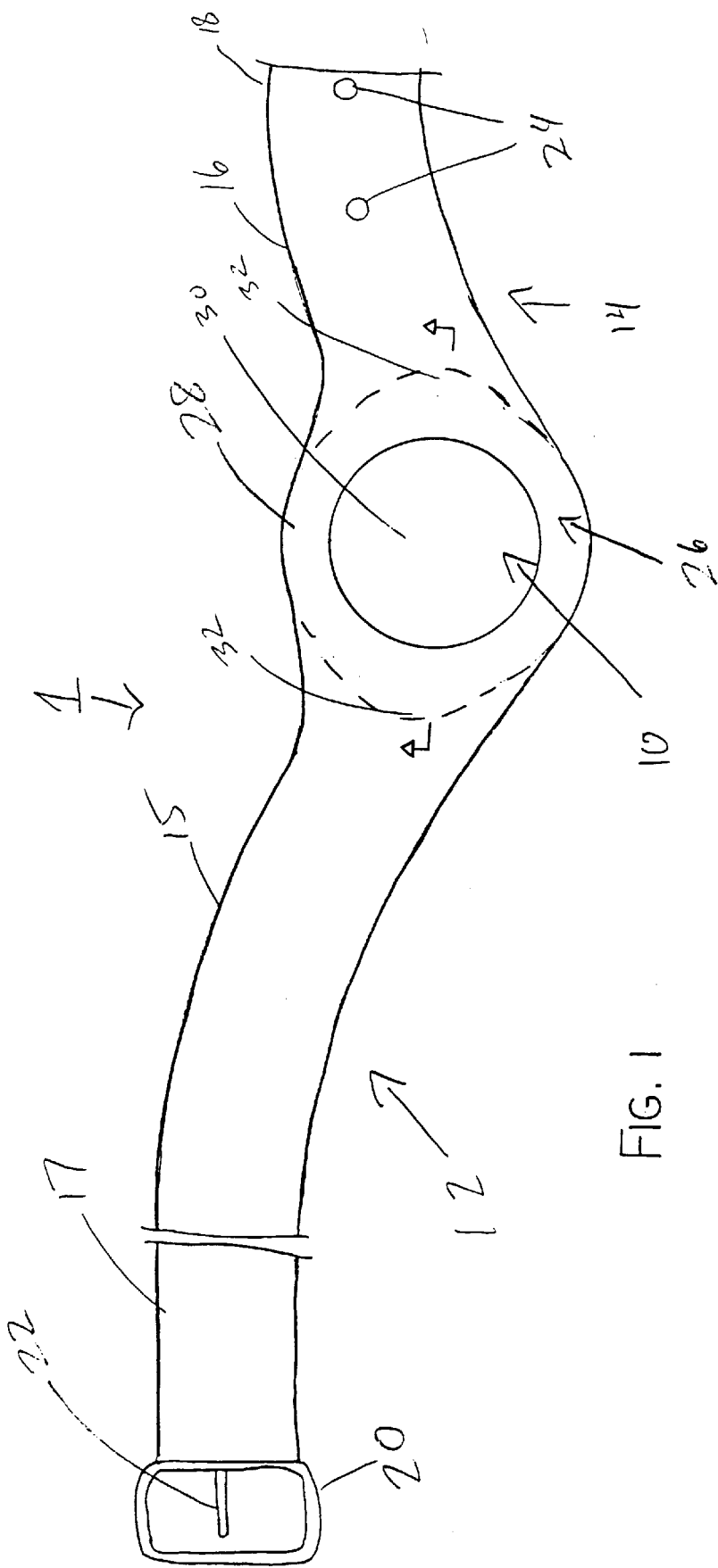
FIG. 1 is a top plan view of the ostomy belt.
Figure 2:
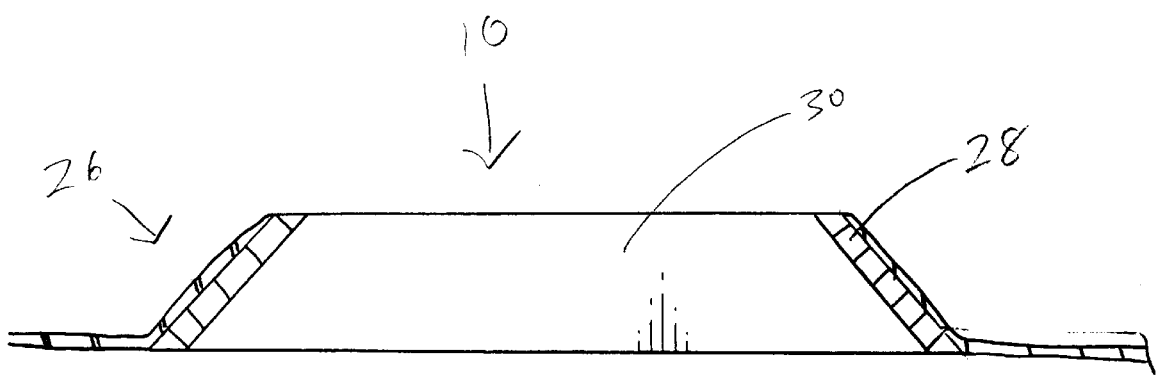
FIG. 2 is a side view in cross section of the support plate.
Figure 4:
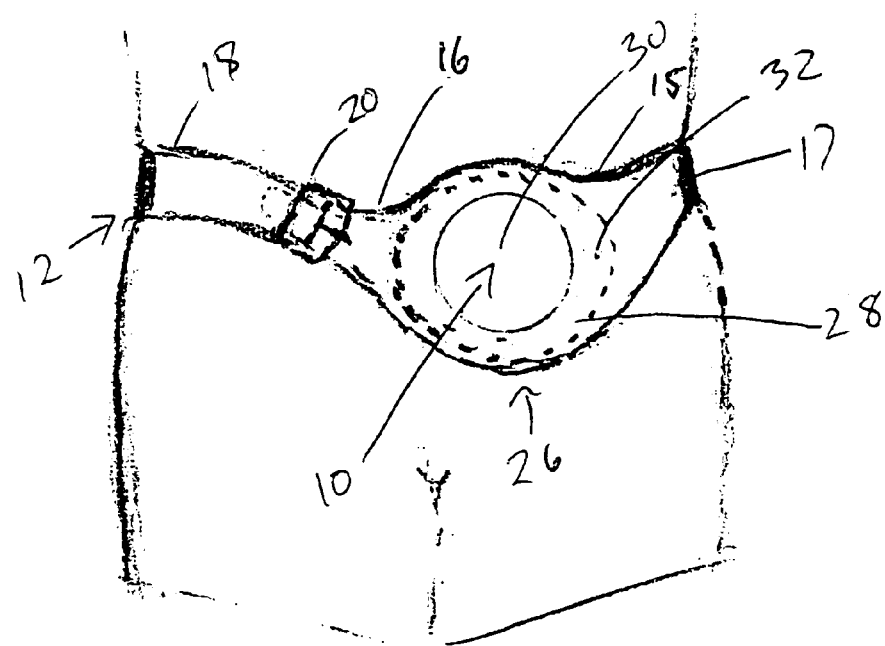
FIG. 4 is a front view of the ostomy belt in use on the left side.

Referring to the drawings, an ostomy belt 1 comprises an open portion 10, a first belt portion 12 and a second belt portion 14. In this embodiment, the ostomy belt 1 is composed of leather. As will be appreciated by one skilled in the art, other suitable materials may also be used. Specifically, the first belt portion 12 and the second belt portion 14 include angled portions 15, 16 which extend outwardly from the open portion 10 at an angle and straight portions 17, 18 which extend from the angle portions 15, 16 respectively, as shown in FIG. 1. Furthermore, straight portion 17 includes a buckle 20 and a prong 22 and straight portion 18 includes a plurality of holes 24 for securing the ostomy belt 1 around the waist of an individual, as described below. The open portion 10 is arranged for connecting an ostomy bag thereto and includes a support 26 for securing the ostomy bag and also for supporting the abdominal wall of the individual when the ostomy bag is connected to the ostomy belt 1, as described below. In this embodiment, the support 26 comprises a concave steel plate 28, as shown in FIG. 2. Specifically, the steel plate 28 is mounted onto the ostomy belt 1 such that the plate 28 surrounds the open portion 10, as shown in FIG. 1. In one embodiment, the steel plate 28 is laminated around the open portion 10. Furthermore, the steel plate 28 has an open center region 30 arranged to overlap the open region 10. The steel plate 28 is arranged to be wider on at least one side 32, as shown in FIG. 4 and, as a result of this arrangement, the steel plate 28 provides abdominal support in the region where hernias develop as a result of ostomies, as discussed below. In some embodiments, the steel plate 28 may include a plurality of apertures surrounding the center region 30 for improving the strength and durability of the ostomy belt 1.

Figure 3:
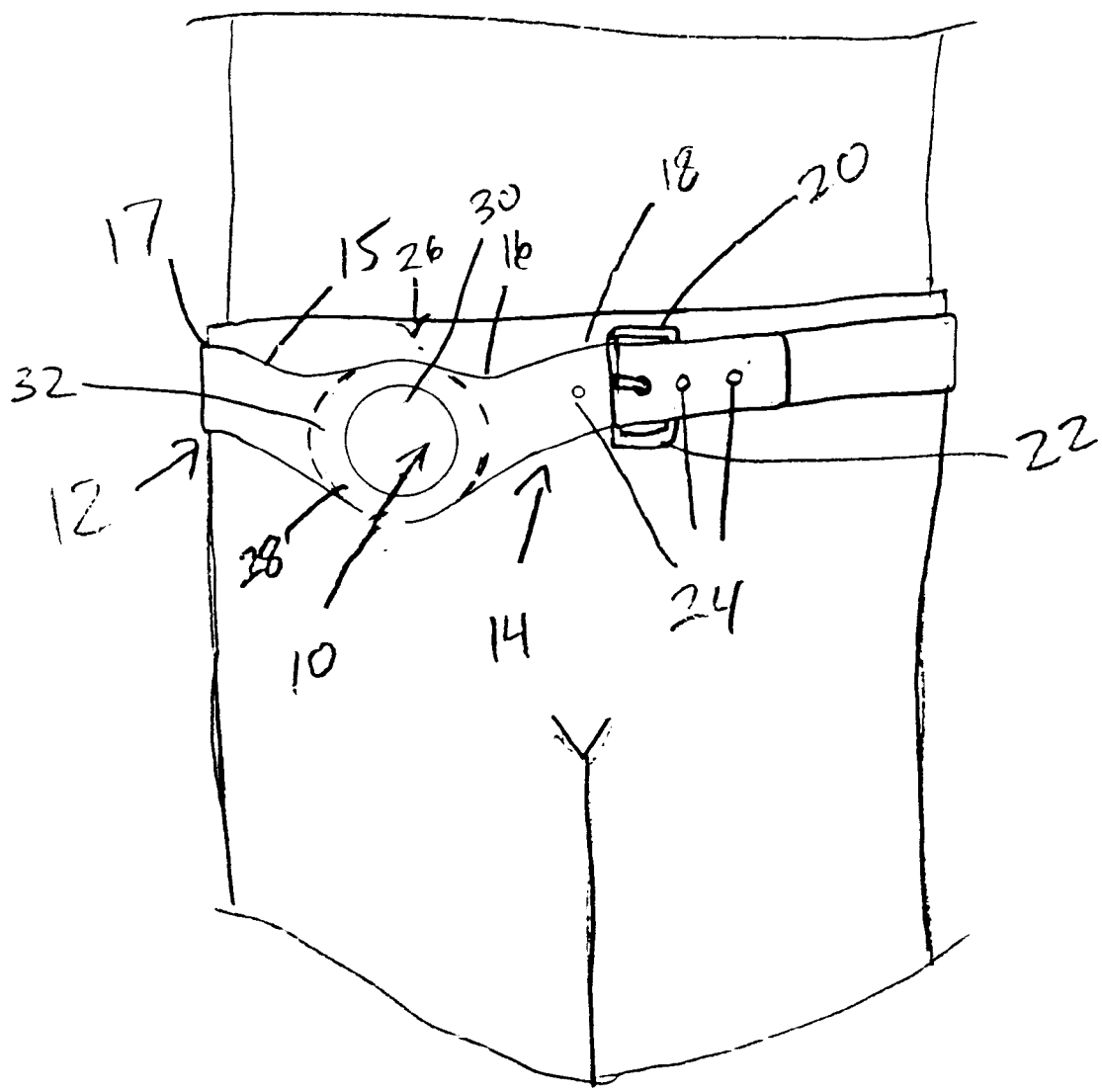
FIG. 3 is a front view of the ostomy belt in use on the right side.

For use, the user grasps the ostomy belt 1 and positions the ostomy belt 1 on their body such that the open portion 10 surrounds the opening in the abdominal wall. At this time, the steel plate 28 is pressed against the abdomen of the user, thereby supporting the abdomen, as described below. The straight portion 18 is then passed through the buckle 20 until the ostomy belt 1 is securely around the waist of the user. The prong 22 is then passed through the closest one of the plurality of holes 24, thereby securing the ostomy belt 1 around the waist of the user, as shown in FIG. 3.

In use, the user positions the ostomy bag such that fecal material from the opening in the abdominal wall is directed into the ostomy bag. It is of note that the ostomy belt 1 is arranged so that it is comfortable while still providing needed support. Specifically, as the open portion 10 is beneath the plane of the straight portions 17, 18, as shown in FIG. 1, the ostomy belt 1 lies substantially around the waist of the user, thereby allowing for greater freedom of movement compared to devices that are placed around the hips. Furthermore, as the ostomy belt 1 is composed of leather, the ostomy belt 1 will not stretch or deform over time as occurs with devices composed of elastic or other similar materials. However, the ostomy belt 1 is easily adjustable, due to the plurality of holes 26. Finally, the shape and placement of the support plate 28 and the specific arrangement of the ostomy belt 1 means that the abdomen of the user is supported by contact with the support plate 28, meaning that the user is less likely to develop hernias or other complications associated with ostomy bags. Specifically, the ostomy belt 1 and the support plate 28 fit securely around the opening in the abdominal wall and provide rigid support to the abdominal wall and the side 32 of the support plate 28 extends over the region of the abdominal wall where hernias are most likely to develop, thereby providing further support.

In other embodiments, the ends of the ostomy belt 1 may be connected or secured together by means known in the art other than the buckle and prong arrangement described above.

While the preferred embodiments of the invention have been described above, it will be recognized and understood that various modifications may be made therein, and the appended claims are intended to cover all such modifications which may fall within the spirit and scope of the invention.

What is claimed is:

1. A method comprising:

providing a belt having an opening and a steel annular plate mounted onto the belt such that the annular plate surrounds the opening:

fitting the belt around the waist of an individual having a stoma opening in a region of the individual's abdominal wall;

positioning the belt con the individual such that the opening surrounds the stoma opening;

supporting the abdominal wall of the individual by tightening the belt such that the steel plate contacts and presses firmly against the region of the abdominal wall surrounding the stoma opening, thereby providing continuous rigid resistance against the abdominal wall and preventing hernia formation; and connecting an ostomy bag to the stoma opening.

* * * * *